(12) United States Patent
Wollschläger

(10) Patent No.: US 6,805,688 B2
(45) Date of Patent: Oct. 19, 2004

(54) METHOD AND DEVICE FOR USE IN MICRO-INVASIVE SURGICAL PROCEDURES, AND GUIDE CATHETER AND VALVE UNIT FOR A DEVICE FOR USE IN MICRO-INVASIVE SURGICAL PROCEDURES

(76) Inventor: Helmut Wollschläger, Gabrielistrasse 9, D-90480 Nürnberg (DE)

( * ) Notice: Subject to any disclaimer, the term of this patent is extended or adjusted under 35 U.S.C. 154(b) by 223 days.

(21) Appl. No.: 09/990,342

(22) Filed: Nov. 23, 2001

(65) Prior Publication Data

US 2002/0065487 A1 May 30, 2002

Related U.S. Application Data

(60) Provisional application No. 60/262,659, filed on Jan. 22, 2001, and provisional application No. 60/253,749, filed on Nov. 29, 2000.

(51) Int. Cl.$^7$ ............................................. A61M 5/178
(52) U.S. Cl. .............................. 604/167.01; 604/167.03
(58) Field of Search ................................ 604/533, 534, 604/535, 536, 537, 538, 539, 284, 93.01, 96.01, 99.04, 164.02, 164.13, 167.01–167.06, 264, 523; 606/191–192, 194

(56) References Cited

U.S. PATENT DOCUMENTS 5,167,239 A * 12/1992 Cohen et al. ............... 600/585
5,336,252 A * 8/1994 Cohen ......................... 607/119
5,624,396 A * 4/1997 McNamara et al. ...... 604/93.01
5,997,562 A    12/1999 Zadno-Azizi et al.

FOREIGN PATENT DOCUMENTS

DE         19823064       11/1999
JP          9225035        9/1997

OTHER PUBLICATIONS

US 5,520,663, 5/1996, Patterson et al. (withdrawn)

* cited by examiner

Primary Examiner—Michael J. Hayes
Assistant Examiner—Catherine S. Williams
(74) Attorney, Agent, or Firm—Stevens, Davis, Miller & Mosher, LLP

(57) ABSTRACT

In a method and a device for use in micro-invasive surgical procedures, and a guide catheter and a valve unit for use in micro-invasive surgical procedures, a bypass section (5) having an enlarged hydraulic cross section is provided, into which an instrument (10), for example a balloon, on an instrument catheter (11) can be retracted after treatment has been administered, thus allowing a sufficient quantity of fluid to flow past the instrument (1) and out of the guide catheter (4). By providing the bypass section (5) with an enlarged cross section, it becomes possible to use instruments (10) with very close-fitting guide catheters (4).

11 Claims, 18 Drawing Sheets

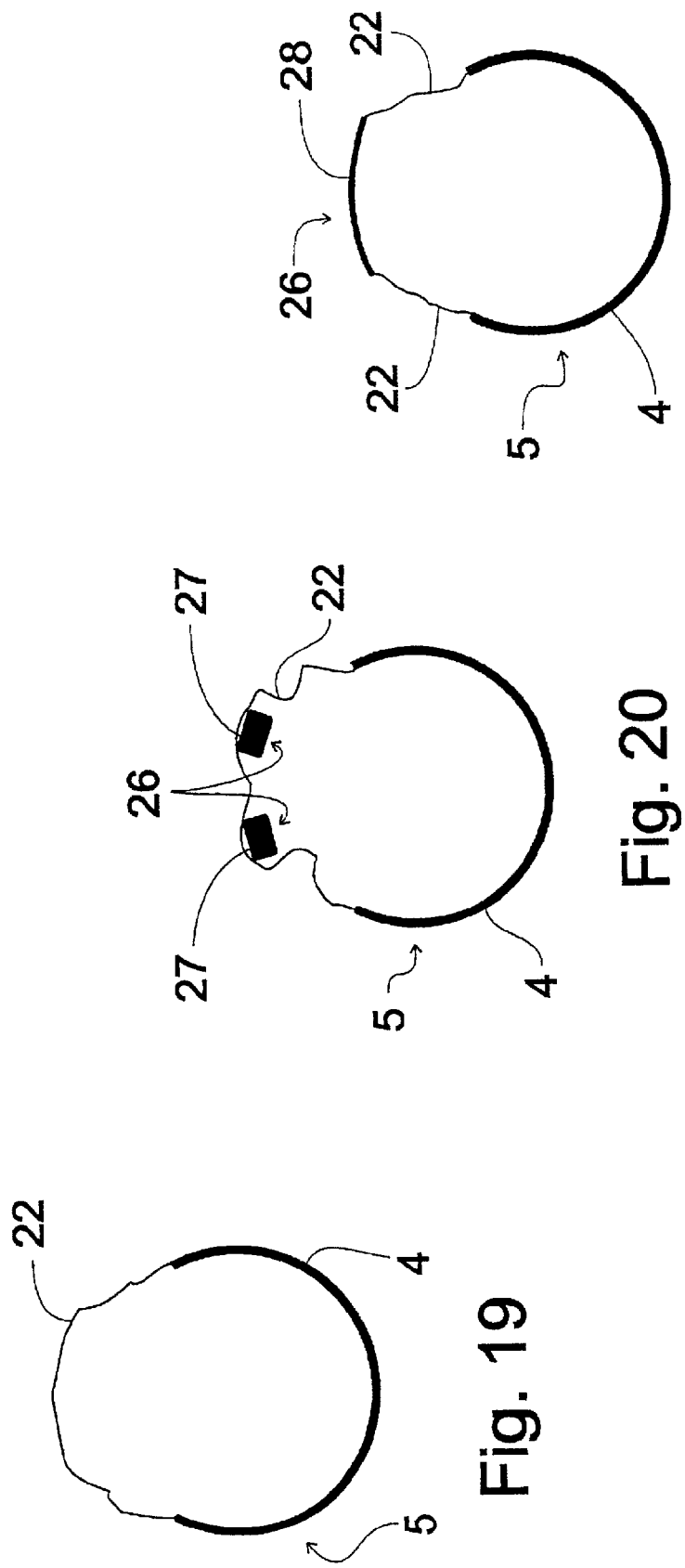

METHOD AND DEVICE FOR USE IN MICRO-INVASIVE SURGICAL PROCEDURES, AND GUIDE CATHETER AND VALVE UNIT FOR A DEVICE FOR USE IN MICRO-INVASIVE SURGICAL PROCEDURES

CROSS REFERENCES TO RELATED APPLICATIONS

This claims priority under 35 USC § 119 from U.S. provisional patent applications Ser. No. 60/253,749 filed Nov. 29, 2000 and Ser. No. 60/262,659 filed Jan. 22, 2001, both incorporated herein by reference.

BACKGROUND OF THE INVENTION

The invention relates to a method for use in micro-invasive surgical procedures, wherein an instrument catheter, which is fitted with an instrument, can be slid within a close-fitting guide catheter in the body of a patient, up to an area in which a diagnostic and/or therapeutic procedure is to be performed.

The invention further relates to a device for use in micro-invasive surgical procedures, comprising a valve unit and a guide catheter that can be connected to the valve unit, into which an instrument catheter, which is fitted with an instrument, can be inserted through the valve unit.

The invention further relates to a guide catheter for a device for use in micro-invasive surgical procedures, into which an instrument catheter, which is fitted with an instrument, can be inserted through a valve unit in the device.

The invention further relates to a valve unit for a device for use in micro-invasive surgical procedures, which can be attached to a guide catheter, into which an instrument catheter, which is fitted with an instrument, can be inserted through the valve unit.

A device of this type, a guide catheter of this type, and a valve unit of this type are known in the art, for example, from DE 198 23 064 C2. The state-of-the-art device is equipped with a valve unit that can be connected to a guide catheter, in which process a dilation catheter as the instrument catheter is inserted through the valve unit into the guide catheter along a guide wire. The dilation catheter is equipped with an expandable balloon as its instrument, which, after being pushed out through the distal end of the guide catheter, can be used to treat vasoconstrictions via dilation. However, the known device, the known guide catheter, and the known valve unit that is used with a known device or a known guide catheter have the disadvantage that in order to permit a sufficient quantity of fluid, such as contrast medium for vasography, to pass through, the outer diameter of the guide catheter must be relatively large, and the outer diameter of the insertion valve must be increased accordingly, which results in a relatively high degree of trauma at the point of entry into a blood vessel.

BRIEF SUMMARY OF THE INVENTION

The object of the invention is to provide a method, a device, a guide catheter, and a valve unit of the type described at the beginning that will make it possible to introduce a sufficient quantity of fluid into the vascular region to be handled or treated in diagnostic or therapeutic micro-invasive surgical procedures, while the outer diameter of the guide catheter is kept relatively small.

This object is attained in accordance with the invention with a method of the type described above, in that during the micro-invasive surgical procedure, the instrument is positioned within a bypass section, whose hydraulic cross section is larger than the cross section of the guide catheter lumen, and whose length corresponds to at least the length of the instrument; and in that a fluid is introduced into the guide catheter along the instrument that is positioned within the bypass section.

This object is attained in accordance with the invention with a device, a guide catheter, and a valve unit of the type described at the beginning, in that a hydraulic bypass section is provided, wherein, while at least part of the guide catheter wall is close-fitting for the instrument, and the lumen cross section corresponds basically to the largest cross section of the instrument, the hydraulic cross section of the bypass section is larger than the lumen cross section, and its length corresponds to at least the length of the largest cross section of the instrument.

Since the invention provides for a bypass section having a hydraulic cross section that is larger than the remaining lumen cross section of the guide catheter, at least in the area of the instrument, which may be a dilatable balloon, a vascular cutter also known as a "rotablator," or some other diagnostic or therapeutic instrument, part of which is larger in its cross section than a guide shaft of the instrument catheter, while the length of this hydraulic cross section corresponds to at least the length of the largest cross section of the instrument, it is now possible to introduce a quantity of fluid, such as a contrast medium that is sufficient for imaging procedures, a solution that contains some active ingredient, or gaseous carbon dioxide, into the vessel that is to be handled or treated, after the instrument has been retracted into the bypass section, even in cases in which the guide catheter lies very close to the instrument, without requiring that the instrument catheter be removed from the valve unit or retracted into the valve unit. This makes treatment through micro-invasive surgery substantially easier.

A further improvement on the device specified in the invention advantageously provides for the bypass section to be an integral part of the guide catheter.

In accordance with one embodiment of the above-mentioned further improvement on the device specified in the invention, it is advantageously provided that the bypass section is positioned in the area of the proximal end of the guide catheter.

In accordance with another embodiment of the above-named further improvement on the device specified in the invention, the bypass section, which may also be designed, for example, as a separate attachment that is integrated into the guide catheter, is positioned advantageously between the proximal end and the distal end of the guide catheter.

In one implementation of the above-named embodiment of the device specified in the invention, the bypass section is advantageously designed to have a reinforcement structure.

In a further improvement on the latter implementation of the device specified in the invention, the reinforcement structure can be expanded in conjunction with the guide catheter wall in the area of the bypass section.

In one arrangement of the bypass section between the proximal end and the distal end of the guide catheter, when a pre-expanded bypass section is used, in other words a bypass section that is expanded prior to its initial use or even during its production, and that cannot be compressed completely to correspond to the remaining outside diameter of the guide catheter, it is advantageous for the bypass section to comprise an insertion valve that is radially flexible. In this manner, when the guide catheter is passed through the insertion valve, only a brief expansion of the trauma caused by the insertion valve is produced, while the increase in the risk of hemorrhaging is insignificant.

In a further implementation of the above-named embodiment of the device specified in the invention, the bypass section is advantageously designed to have a bypass sheath that encloses the guide catheter, is sealed at its edges, and is attached to the wall of the guide catheter; and to have recesses that are built into the wall of the guide catheter near the edges of the bypass sheath.

In the latter implementation, in one form of the implementation, the recesses are essentially rounded in cross section, or are rectangular in cross section, with the lengths of the sides being essentially equal.

In a further implementation of the above-named embodiment of the device specified in the invention, the bypass section is advantageously designed to have a number of grooves that extend through the wall of the guide catheter, wherein the grooves are sealed with an outer sheath.

In one embodiment of the latter implementation of the device specified in the invention, which is equipped with the aforementioned grooves, the grooves are oriented lengthwise along the guide catheter.

In another embodiment of the latter implementation of the device specified in the invention, which is equipped with the aforementioned grooves, the grooves are designed to be coiled in a spiral.

In one device specified in the invention, in which the bypass section is positioned between the proximal end and the distal end of the guide catheter, a further embodiment advantageously provides that the wall of the guide catheter is equipped with a recessed area, in the area of the bypass section, with this recessed area extending essentially over the entire length of the bypass section, and that a collapsible bypass sheath is attached to the wall of the guide catheter, and serves to seal the recess in the wall.

In the latter embodiment it is further advantageous, for purposes of stability, for the device to contain a sheath frame unit that extends lengthwise along the guide catheter, and which can be placed in an inward, engaged position or in an outward, disengaged position.

In one implementation of the latter embodiment having a sheath frame unit, it is provided that the sheath frame unit is comprised of at least two frame braces, the outer surface area of which is small relative to the radial dimensions of the recess in the wall.

In a further implementation of the latter embodiment having a sheath frame unit, it is provided that the sheath frame unit is comprised of one frame membrane, the outer surface area of which is large relative to the radial dimensions of the recess in the wall.

In the further improvement on the device specified in the invention having a bypass section that is integrated into the guide catheter, and is positioned between the proximal end and the distal end of the guide catheter, and in the related implementations, it is advantageously provided in one exemplary embodiment that edge markers are included along the edges of the bypass section for use in imaging procedures.

In the further improvement on the device specified in the invention having a bypass section that is integrated into the guide catheter and is positioned between the proximal end and the distal end of the guide catheter, and the associated implementations of this device, it is advantageously provided in a further exemplary embodiment that visible or palpable markers are provided, which can be seen or felt during positioning of the instrument in the bypass section.

In another further improvement on the device specified in the invention, it is advantageously provided that the bypass section is designed to form a single unit together with the valve unit.

In another further improvement on the device specified in the invention, it is advantageously provided that the bypass section is designed as a torsion-proof, flexible or rigid intermediate segment that can be inserted between the guide catheter and the valve unit.

In the latter further improvement on the device specified in the invention, one embodiment advantageously provides that the intermediate segment can be connected to the guide catheter such that it can rotate.

To enable visual control, in the further developments and embodiments, with a bypass section that is positioned in the area of the proximal end of the guide catheter and is designed as a separate, intermediate unit, or as a single unit in conjunction with the valve unit, it is advantageous for the bypass section to have at least one transparent section, or to be completely transparent.

In the latter two further improvements, and in related improvements on the device specified in the invention, the length of the bypass section and the length of the valve unit through which the instrument catheter is inserted, together advantageously correspond to at least the length of a section that slides along the guide wire between the distal end of the instrument and a point of exit for the guide wire on the guide shaft.

In a further improvement on the guide catheter specified in the invention it is advantageously provided that the bypass section is positioned in the area of the proximal end of the guide catheter.

In another further improvement on the guide catheter specified in the invention, it is advantageously provided that the bypass section, which may also be designed, for example, as a separate attachment that is integrated into the guide catheter, is positioned between the proximal end and the distal end of the guide catheter.

In one implementation of the aforementioned embodiment of the guide catheter specified in the invention, the bypass section is advantageously designed to have a reinforcement structure.

In a further improvement on the latter implementation of the guide catheter specified in the invention, it is further advantageously provided that the reinforcement structure can be expanded in conjunction with the guide catheter wall in the area of the bypass section.

In a further implementation of the latter further improvement on the guide catheter specified in the invention, the bypass section is designed to have a bypass sheath that encompasses the guide catheter and is connected to the wall of the guide catheter and sealed at the edges; and to have recesses built into the wall of the guide catheter in the area of the edges of the bypass sheath.

In the latter implementation, in one exemplary embodiment the recesses are essentially rounded in cross section, or are rectangular in cross section, with the lengths of the sides being essentially equal.

In a further implementation of the latter further improvement on the guide catheter specified in the invention, it is advantageously provided that at least the bypass section is designed to have a number of grooves that extend through the wall of the guide catheter, wherein the grooves are sealed by an outer sheath.

In one implementation of a guide catheter having grooves, as specified in the invention, the grooves are oriented lengthwise along the guide catheter.

In a further implementation of a guide catheter having grooves, as specified in the invention, the grooves are coiled in a spiral.

In one guide catheter as specified in the invention, in which the bypass section is positioned between the proximal end and the distal end of the guide catheter, it is advantageously provided in one further embodiment that the wall of the guide catheter is equipped with a recessed area, in the area of the bypass section, with this recessed area extending essentially over the entire length of the bypass section, and that a collapsible bypass sheath is attached to the wall of the guide catheter, and serves to seal the recess in the wall.

In the latter embodiment of a guide catheter as specified in the invention it is further advantageous, for purposes of stability, for the device to contain a sheath frame unit that extends lengthwise along the guide catheter, and which can be placed in an inward, engaged position or in an outward, disengaged position.

In one embodiment, the sheath frame unit is comprised of at least two frame braces, the outer surface area of which is small relative to the radial dimensions of the recess in the wall.

In a further embodiment, the sheath frame unit is comprised of one frame membrane, the outer surface area of which is large relative to the radial dimensions of the recess in the wall.

In the further improvement on the guide catheter specified in the invention that has a bypass section that is positioned between the proximal end and the distal end of the guide catheter, edge markers are advantageously provided along the edges of the bypass section for use in imaging procedures.

In one embodiment of the valve unit specified in the invention, it is provided that the bypass section is designed to form a single unit with the valve unit.

In another embodiment of the valve unit specified in the invention it is provided that the bypass section is designed as an intermediate segment that is connected to the valve unit such that it can be removed.

In a further improvement on the latter embodiment of the valve unit specified in the invention, the intermediate segment can be advantageously connected to a guide catheter such that the segment can rotate.

In a further improvement on the method specified in the invention it is advantageously provided that the expanded hydraulic cross section is created by an instrument, designed to be a dilatable balloon. In this manner, the bypass section can be expanded when it is already inside the body of a patient, after being introduced through an insertion valve, which is relatively rigid, and whose size corresponds to the outer cross section of the guide catheter.

BRIEF DESCRIPTION OF THE DRAWINGS

Further advantageous embodiments and advantages of the invention are the object of the following description of exemplary embodiments, with reference to the figures in the diagrams.

These show.

DETAILED DESCRIPTION

Figure 1:
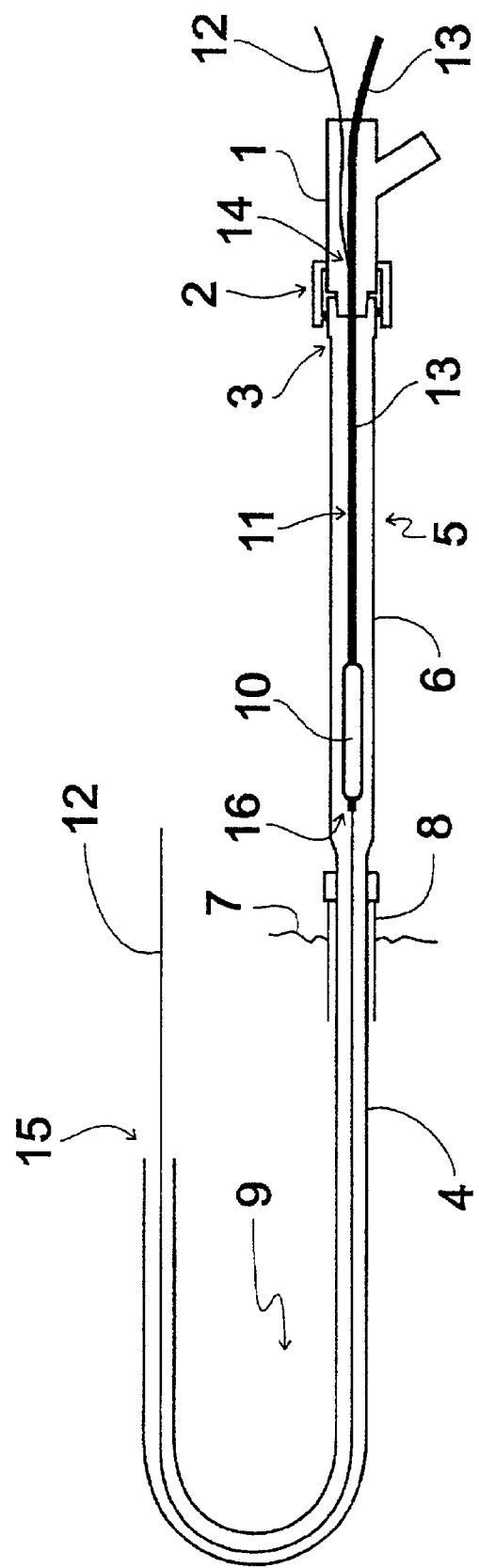
FIG. 1 a partial side view cross section of a first exemplary embodiment of the invention having a bypass section that is positioned at the proximal end of a guide catheter.

FIG. 1 shows a first exemplary embodiment of the invention in a partial side view cross section. The device as illustrated in FIG. 1 is equipped with a valve unit 1, which in the initial exemplary embodiment is a state-of-the-art, so-called Y-valve. The valve unit 1 can be connected via a rotating coupling 2 to a proximal end 3 of a guide catheter 4 in the device. In the area of the proximal end 3 of the guide catheter 4, a bypass section 5, which has an enlarged hydraulic cross section, is positioned as the proximal end section 6 of the guide catheter 4. The guide catheter 4 can be inserted through a tissue wall 7 using an insertion valve 8, wherein, when the device is used as intended, a section 9 that is positioned inside the body has an inner diameter that is smaller than the inner diameter at the proximal end section 6 of the guide catheter 4. The device as illustrated in FIG. 1 is equipped with an expandable balloon 10 as a non-exclusive example of an instrument, which is connected via known means to an instrument catheter that is designed as a dilation catheter 11. The inner diameter of the inner-corporal section 9 corresponds generally to the outer diameter of the balloon 10, which is equipped with a guide wire 12 and a guide shaft 13 that is positioned at the proximal end of the balloon 10, wherein a certain length of the guide wire 12 extends inside the guide shaft 13, emerging from the guide shaft 13 at a point of exit 14.

In accordance with the requirements of the known, micro-invasive surgical technique of vasodilation in which an expandable balloon 10 is used, as a non-exclusive example of a micro-invasive surgical procedure, the valve unit 1, the coupling 2, and the insertion valve 8 are arranged such that when the corresponding insertion points have been sealed, the guide wire 12 can be pushed beyond the distal end 15 of the guide catheter 4, into the vascular region to be dilated. After the guide wire 12 has been positioned, the balloon 10 can be introduced into the guide catheter 4 through the valve unit 1 by advancing the guide shaft 13 along the guide wire 12, and can be advanced along the inner-corporal section 9 up to the vascular region that is to be dilated.

After dilation of the vascular region to be treated has been performed by w expanding the balloon 10, the balloon 10 can be retracted into the bypass section 5, wherein the bypass section 5 and the section of the valve unit 1 that takes up the guide wire 12 and the guide shaft 13 together have a length that is greater than the distance between the distal end 16 of the balloon 10 and the point of exit 14. Now, a fluid, such as a solution that contains some active ingredient, gaseous carbon dioxide, or a contrast medium can be introduced into the valve unit 1 via known methods, flowing past the balloon 10, through the inner-corporal section 9 of the guide catheter 4, and into the vascular area that is to be dilated, without requiring that the dilation catheter 11, part of which lies between the point of exit 14 and the distal end 16 of the balloon 10, be removed from the valve unit 1 or retracted into the valve unit 1. Thus, for example, after the success of the dilation has been evaluated, the balloon 10 can again be easily advanced through the inner-corporal section 9 of the guide catheter 4 into the vascular area that is to be dilated, to allow further dilation if required.

Figure 2:
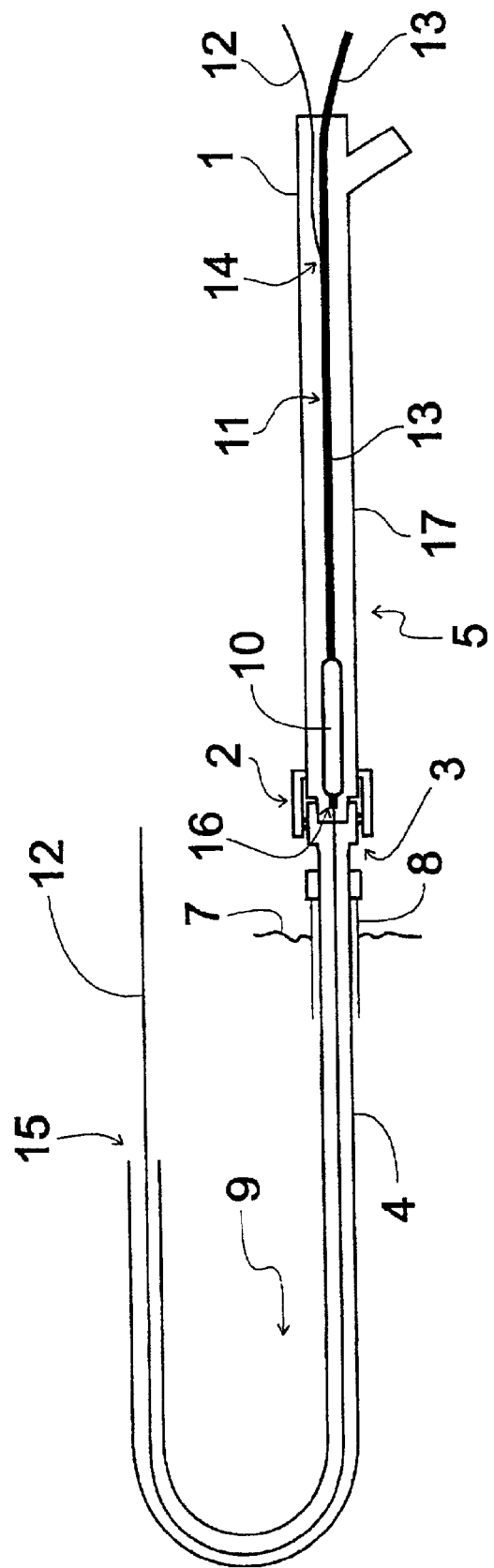
FIG. 2 a partial side view cross section of a secondary exemplary embodiment of the invention, having a bypass section that is designed to form a single unit with a valve unit.

FIG. 2 shows a partial side view cross section of a secondary exemplary embodiment of a device as specified in the invention, wherein elements that correspond to those in the initial exemplary embodiment as illustrated in FIG. 1 and in the secondary exemplary embodiment as illustrated in FIG. 2 are assigned the same reference numbers, and are not discussed further here. In the secondary exemplary embodiment as illustrated in FIG. 2, the bypass section 5 is designed to form a single unit with the valve unit 1, as the end section 17 of the valve unit, having an inner diameter that is greater than the inner diameter of the inner-corporal section 9, which corresponds to the outer diameter of the uninflated balloon 10, wherein the coupling 2 is now positioned at the distal end of the distal end section 17. The length of the distal end section 17 and the section of the valve unit 1 that lies in the extension of the distal end section 17, is such that the dilation catheter 11, with its section that lies between the distal end 16 of the balloon 10 and the point of exit 14, lies within the distal end section 17 and the valve unit 1. Hence, use of this embodiment is basically the same as with the initial exemplary embodiment as illustrated in FIG. 1.

Figure 3:
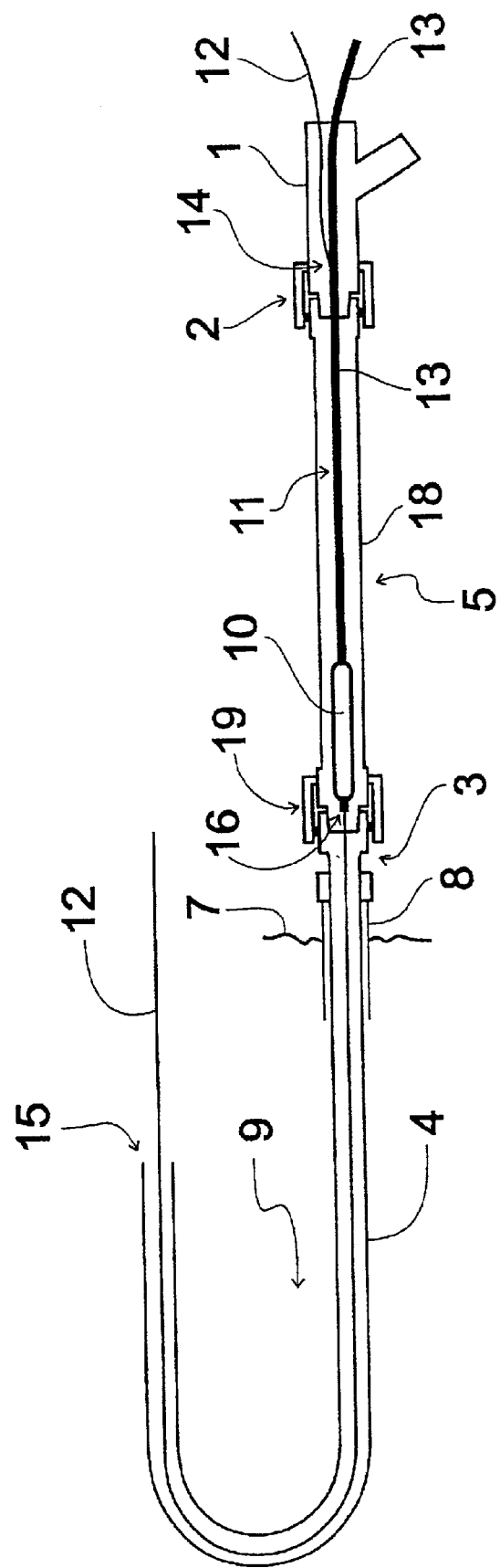
FIG. 3 a partial side view cross section of a third exemplary embodiment of the invention, having a bypass section that is designed as a separate intermediate segment.

FIG. 3 shows a partial side view cross section of a third exemplary embodiment of a device as specified in the invention, wherein corresponding elements from the initial exemplary embodiment as illustrated in FIG. 1, from the secondary exemplary embodiment as illustrated in FIG. 2, and from the third exemplary embodiment as illustrated in FIG. 3 are assigned the same reference numbers, and are not described further. In the third exemplary embodiment in accordance with FIG. 3, the bypass section 5 is designed as a separate intermediate segment 18 that in this exemplary embodiment is torsion-free, and can be connected to the preferably rotatable coupling 2 of the valve unit 1, as well as to the proximal end 3 of the guide catheter, via an intermediate coupling 19. As with the preceding exemplary embodiments, the intermediate segment 18 has an inner diameter that is greater than the inner diameter of the inner-corporal section 9 of the guide catheter 4, which corresponds to the outer diameter of the undilated balloon 10. In addition, the length of the intermediate segment 18 is such that the section that lies between the distal end 16 of the balloon 10 and the point of exit 14 can be positioned entirely within the intermediate segment 18 and the section of the valve unit 1 that lies within the extension.

In the third exemplary embodiment as illustrated in FIG. 3, the intermediate coupling 19 preferably forms a rotating connection between the guide catheter 4 and the intermediate segment 18, wherein the guide catheter 4 can be rotated around a swivel nut that is rigidly attached to the catheter. Use of the third exemplary embodiment is basically the same as with the initial exemplary embodiment as illustrated in FIG. 1 and the secondary exemplary embodiment as illustrated in FIG. 2.

In the exemplary embodiments described in reference to FIG. 1 through FIG. 3 it is advantageous for the bypass section 5 to be transparent, either entirely or in slit-shaped sections, in order to enable the visual monitoring of the positioning of the balloon 10.

Figure 4:
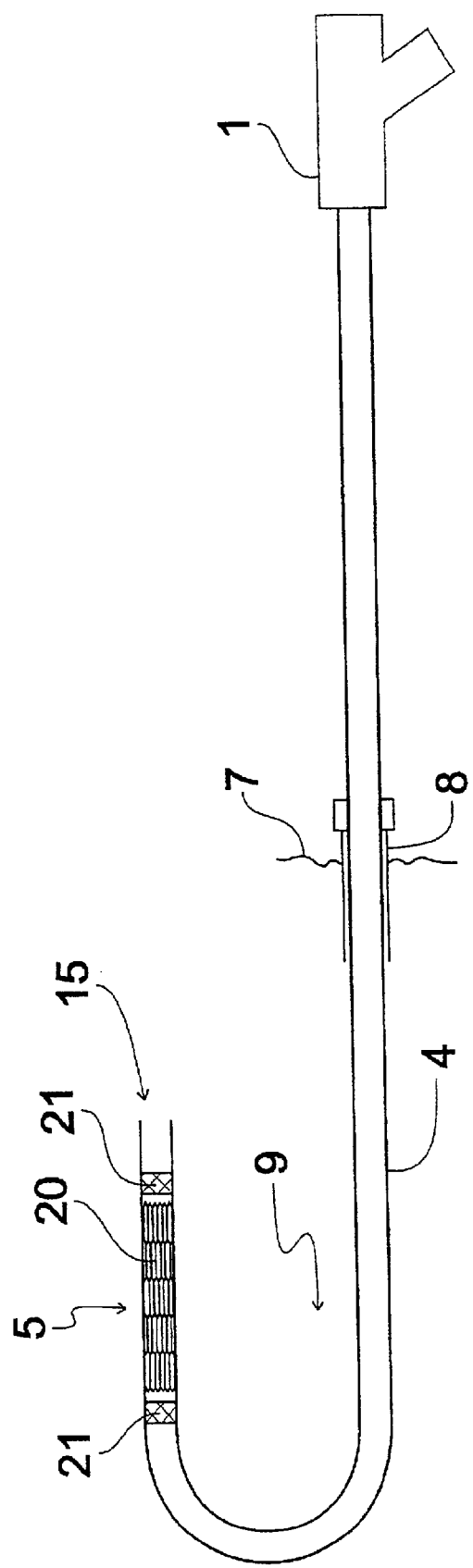
FIG. 4 a partial side view cross section of a fourth exemplary embodiment of the invention, having a bypass section that is positioned in the distal end area of a guide catheter, and is equipped with a reinforcement structure.

FIG. 4 shows a partial side view cross section of a fourth exemplary embodiment of a device as specified in the invention, wherein elements that correspond to elements from the preceding exemplary embodiments are assigned the same reference numbers, and are not discussed further. The device illustrated in FIG. 4 is equipped with a guide catheter 4 at the distal end 15 of which a bypass section 5 is provided, which has an expandable reinforcement structure 20. The reinforcement structure 20 is incorporated into the wall of the guide catheter 4, wherein the wall of the guide catheter 4, at least in the area of the reinforcement structure 20, is designed to be flexible and deformable. The length of the reinforcement structure 20 is greater than the length of the balloon 10, and may be further reinforced using a so-called stent, for example, as is illustrated in FIG. 4. Thus it is advantageous for the entire reinforcement structure 20 to have a limited expansion, with the maximum diameter of the bypass section 5 corresponding at most to the outer diameter of the insertion valve 8.

At the edge of the bypass section 5, edge markers 21 are built into the wall of the guide catheter 4, which clearly mark the ends of the bypass section 5 for use in imaging procedures.

Figure 5:
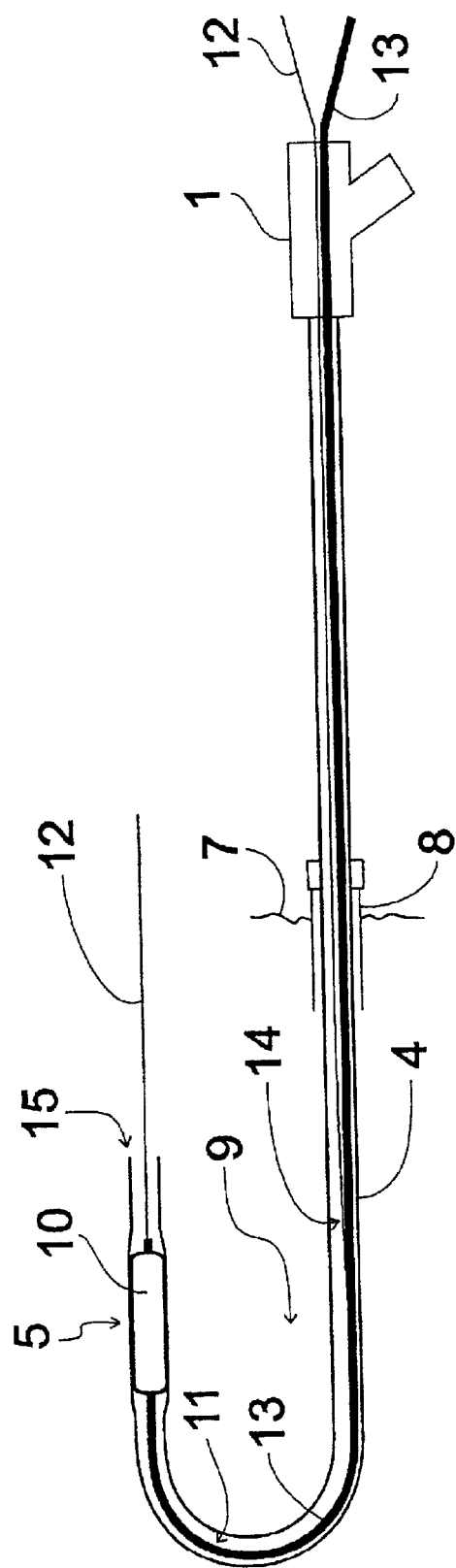
FIG. 5 the exemplary embodiment as illustrated in FIG. 4, having a dilated balloon, positioned in the bypass section, as its instrument.

FIG. 5 shows a partial side view cross section of the fourth exemplary embodiment as illustrated in FIG. 4, having a dilation catheter 11 that has been inserted through the valve unit 1 into the guide catheter 4. In the arrangement illustrated in FIG. 5, the balloon 10 lies inside the reinforcement structure 20 in the bypass section 5, which is not shown in FIG. 5 for purposes of improving clarity of the diagram. In this positioning, the balloon 10 is expanded via known methods, at various positions, so that the guide catheter 4 expands in the area of the bypass section 5 over a length that is greater than the length of the balloon 10.

Figure 6:
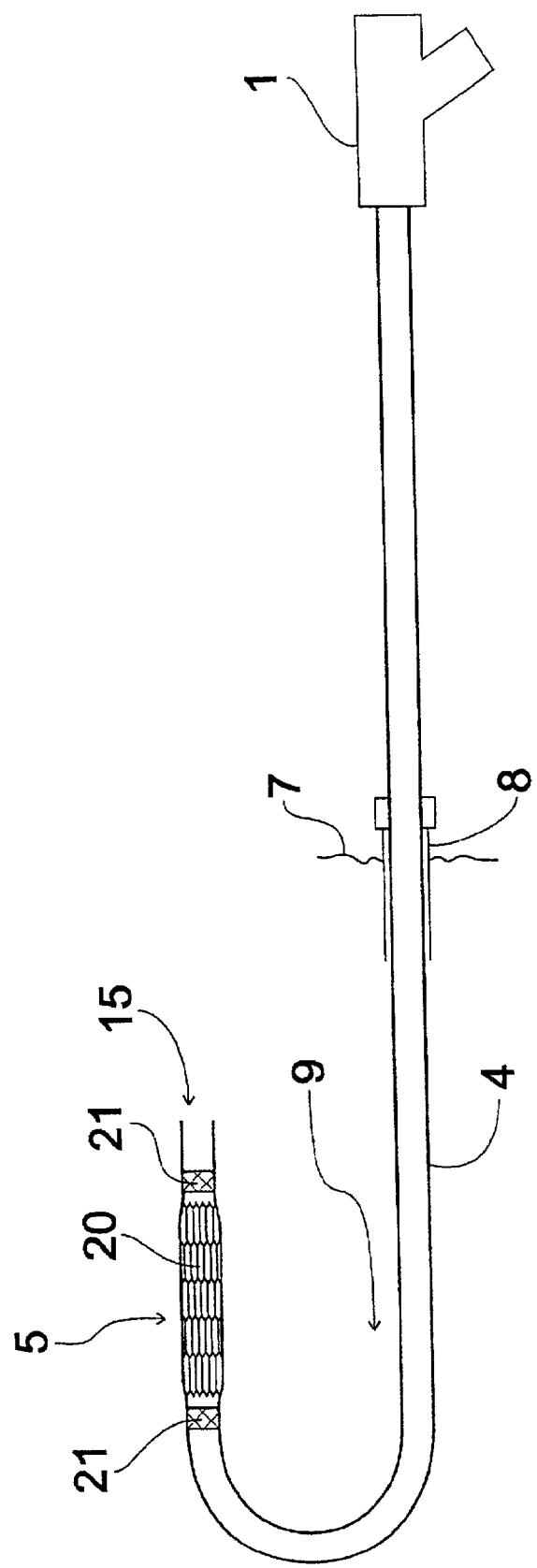
FIG. 6 the bypass section of the exemplary embodiment as illustrated in FIG. 4 and FIG. 5, in which the reinforcement structure is enlarged following dilation of the balloon.

FIG. 6 shows a partial side view cross section of the fourth exemplary embodiment as illustrated in FIG. 4 and FIG. 5, after the balloon 10 has been expanded in the position illustrated in FIG. 5. As can be seen from FIG. 6, the reinforcement structure 20 is now expanded in its cross section, and the wall of the guide catheter 4 has also been expanded. Now, an undilated balloon 10 can be positioned inside the bypass section 5, wherein a quantity of fluid, such as a contrast medium that is sufficient to allow imaging of the vessel that is to be dilated or has already been dilated, is allowed to flow through the stabilized expansion of the reinforcement structure 20 and the wall of the guide catheter 4 into the bypass section 5.

Following completion of the micro-invasive surgical procedures, the guide catheter 4 can be retracted, wherein the guide catheter 4 is removed together with the insertion valve 8, or the outer diameter of the bypass section 5 is initial reduced to its original size, and then is guided through the fixed insertion valve 8; the guide catheter 4 is then drawn out through the insertion valve 8 prior to the removal of the insertion valve 8.

Figure 7:
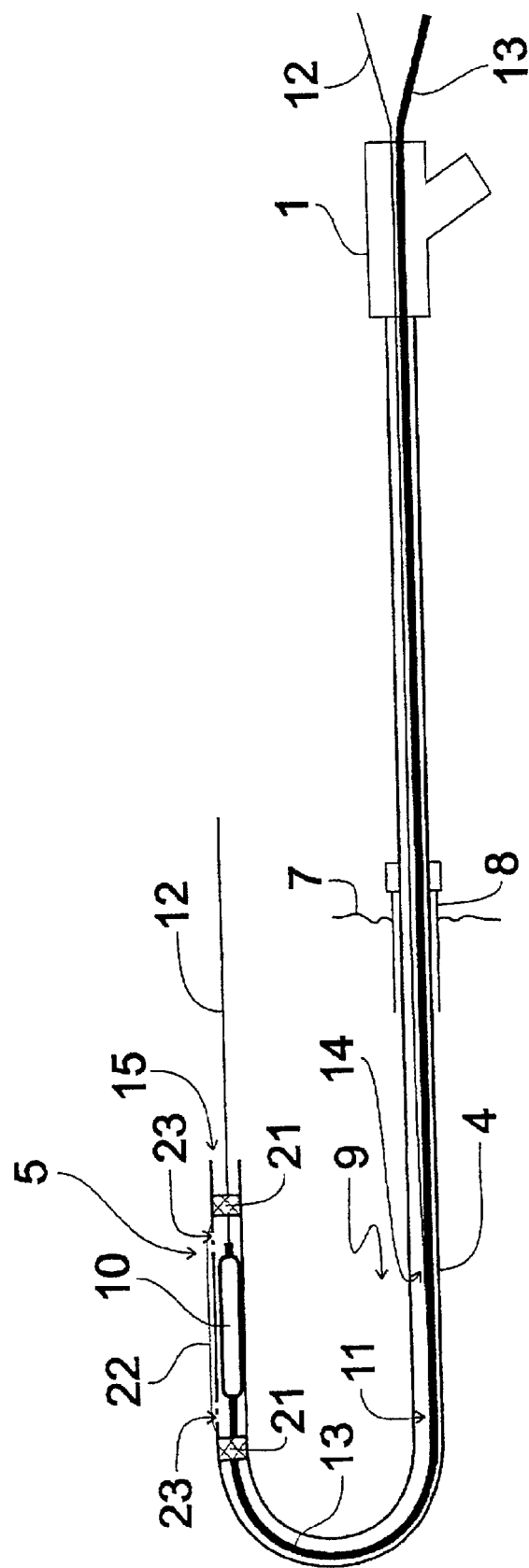
FIG. 7 a partial side view cross section of a fifth exemplary embodiment of the invention, having a bypass section that is positioned in the distal end area of a guide catheter, and is equipped with a bypass sheath.

FIG. 7 shows a partial side view cross section of a fifth exemplary embodiment of a device as specified in the invention, wherein elements of the fifth exemplary embodiment that correspond to elements that are described in the initial exemplary embodiment through the fourth exemplary embodiment are assigned the same reference numbers, and are not discussed further. In the fifth exemplary embodiment as illustrated in FIG. 7, a bypass section 5, which may, for example, be designed as a separate attachment that is integrated into a guide catheter 4, is provided, and is positioned in the area of the distal end 15 of the guide catheter 4. The bypass section 5 in accordance with the fifth exemplary embodiment is equipped with a bypass sheath that at least partially encloses the outer wall, and is attached to the wall at the proximal end and the distal end of the bypass section 5, and is sealed at the edges.

In one embodiment, the bypass sheath 22 is made of a flexible, expandable material. In another embodiment, the bypass sheath 22 is folded, wherein the bypass sheath 22 unfolds when a certain level of pressure has been reached inside the guide catheter 4.

In the area of the distal end and the proximal end of the bypass section 5, a number of recesses 23 are built into the wall of the guide catheter 4, and are designed to connect the inner lumina of the guide catheter 4 with a bypass volume that develops between the wall of the guide catheter 4 and the bypass sheath 22. In this, the recesses 23 that are built into the distal end of the bypass section 5 are separated from the recesses 23 built into the proximal end of the bypass section 5 by a distance that corresponds at least to the length of the balloon 10.

In the fifth exemplary embodiment as illustrated in FIG. 7, the balloon 10 can be retracted into the bypass section 5 following dilation of the vessel, allowing a sufficient quantity of fluid that has been introduced through the valve unit 1 into the inner lumina of the guide catheter 4 to flow through the bypass volume and out of the distal end 15 of the guide catheter 4, into the vessel that is to be treated.

Also in the fifth exemplary embodiment as illustrated in FIG. 7, it is advantageous to provide edge markers 21 that will clearly indicate the end areas of the bypass section 5 to aid in imaging procedures.

Figure 8:
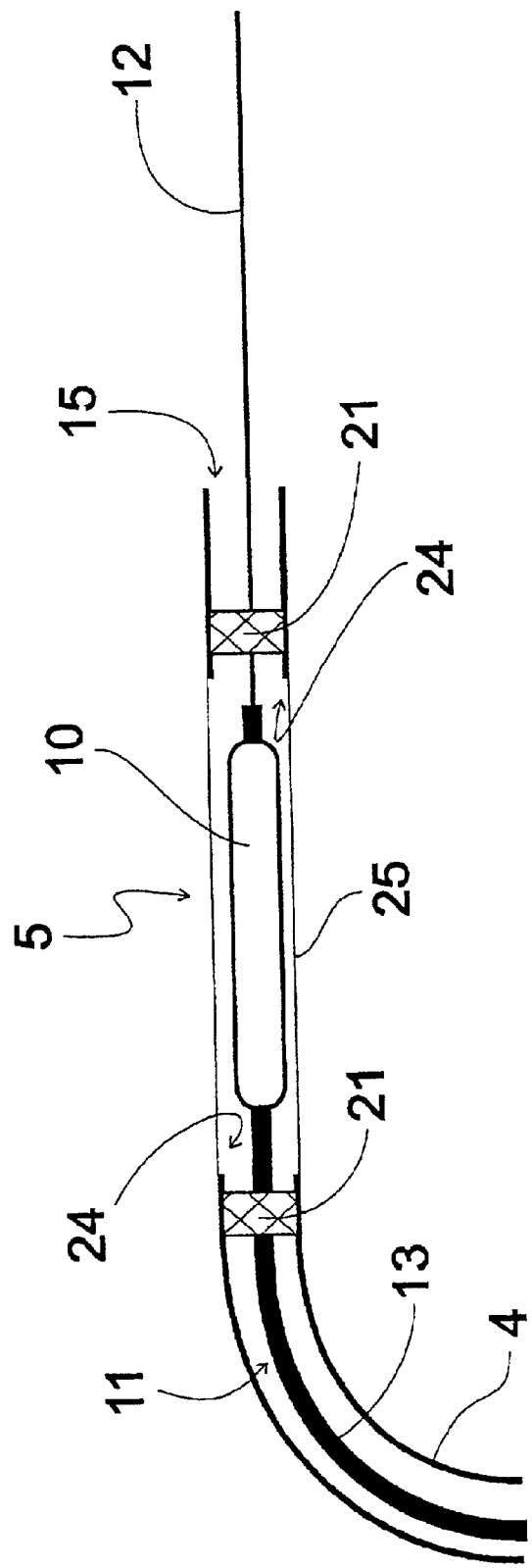
FIG. 8 a partial side view cross section of a section of a sixth exemplary embodiment of the invention, having a bypass section that is designed to have a number of grooves built into the wall of the guide catheter.

FIG. 8 shows a partial side view cross section of a sixth exemplary embodiment of a device as specified in the invention, illustrating a section of the distal end of a guide catheter, wherein elements that correspond to elements discussed in connection with the preceding exemplary embodiments are assigned the same reference numbers, and will not be discussed further. In the sixth exemplary embodiment as illustrated in FIG. 8, the bypass section 5, which is designed, for example, as a separate attachment that is integrated into the guide catheter 4 and has a high degree of rigidity, is positioned in the area of the distal end 15 of the guide catheter 4, and is equipped with grooves 24 that are built into the wall, and extend through the wall; these grooves preferably extend around the entire circumference of the wall, and are oriented lengthwise along the guide catheter 4. The length of the grooves 24 corresponds at least to the length of the balloon 10. The grooves 24 are enclosed on the outside by a thin outer sheath 25, which seals the edges of the bypass section 5.

Figure 9:
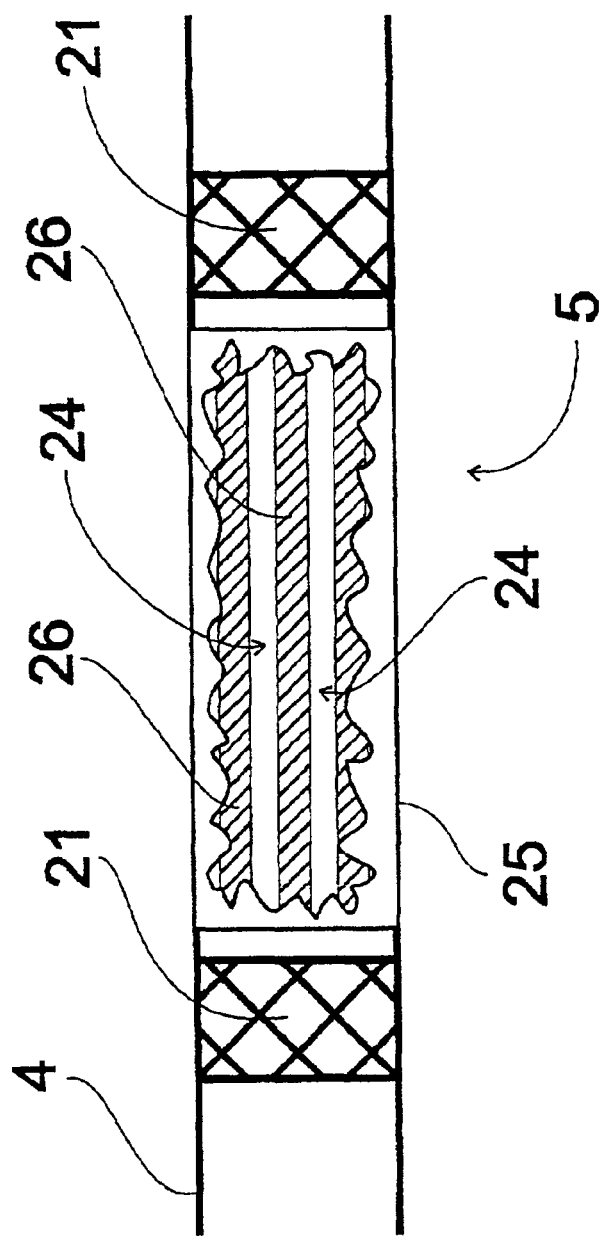
FIG. 9 a section of the guide catheter in the exemplary embodiment as illustrated in FIG. 8, in the area of the bypass section, having an outer sheath, shown here as partially open, which encloses the grooves.

FIG. 9 shows a section of the guide catheter 4 from the exemplary embodiment as illustrated in FIG. 8, in the area of the bypass section 5, with an outer sheath 25, shown here partially open. As can be seen in FIG. 9, bridges 26 are present between the grooves, which support the outer sheath 25 and guarantee adequate rigidity against torsion for the guide catheter 4.

The outer sheath 25 is preferably also connected to the outside surfaces of the bridges 26 that are built up between the grooves 24, and is made to be flexible or folded, thus further increasing the hydraulic cross section.

Figure 10:
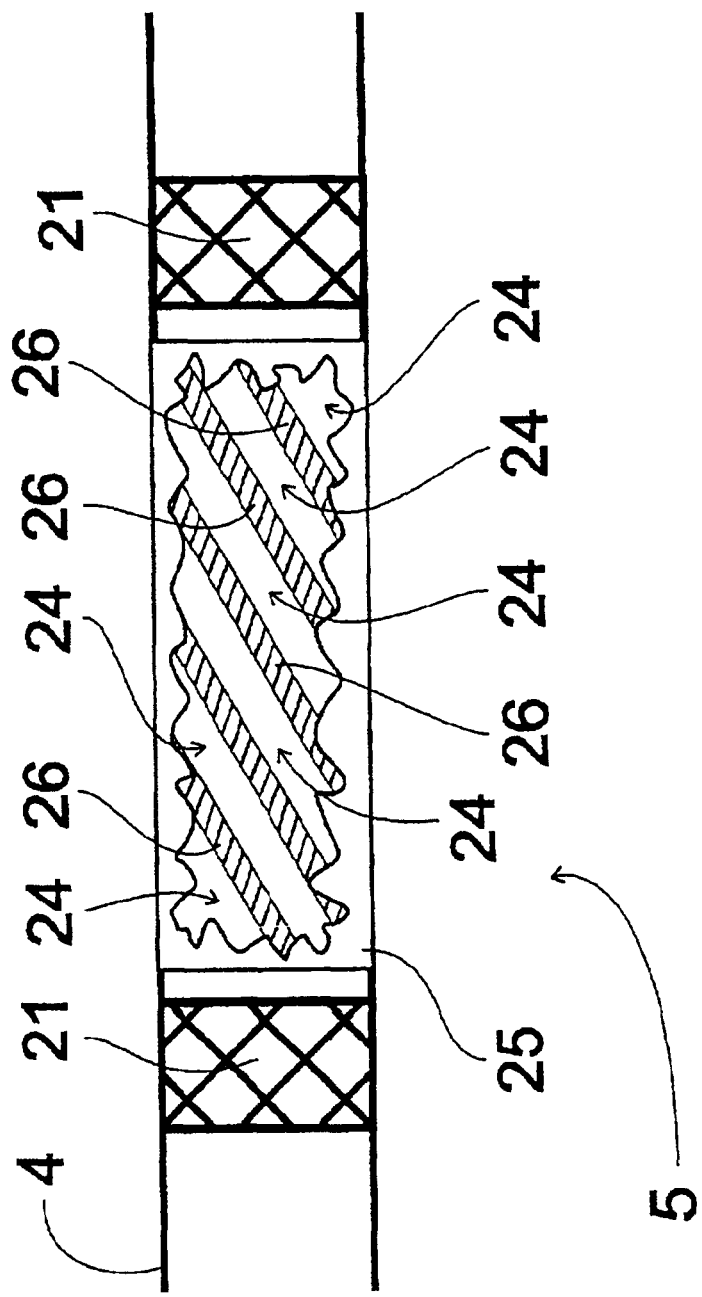
FIG. 10 a section of a guide catheter in a modification on the exemplary embodiment as illustrated in FIG. 8 and FIG. 9, in the area of the bypass section, having an outer sheath, shown here as partially open, which encloses the grooves.

FIG. 10 shows a section of a guide catheter 4 in the area of the bypass section 5, in a modification on the exemplary embodiment as illustrated in FIG. 8, having an outer sheath 25 that is shown here partially open. In the embodiment illustrated in FIG. 10, the grooves 24, and thus also the bridges 26, are designed as spiral coils. This embodiment offers the advantage of reducing the risk that a balloon 10 could remain in the grooves 24 following dilation thus seriously impeding the flow of fluid.

Figure 11:
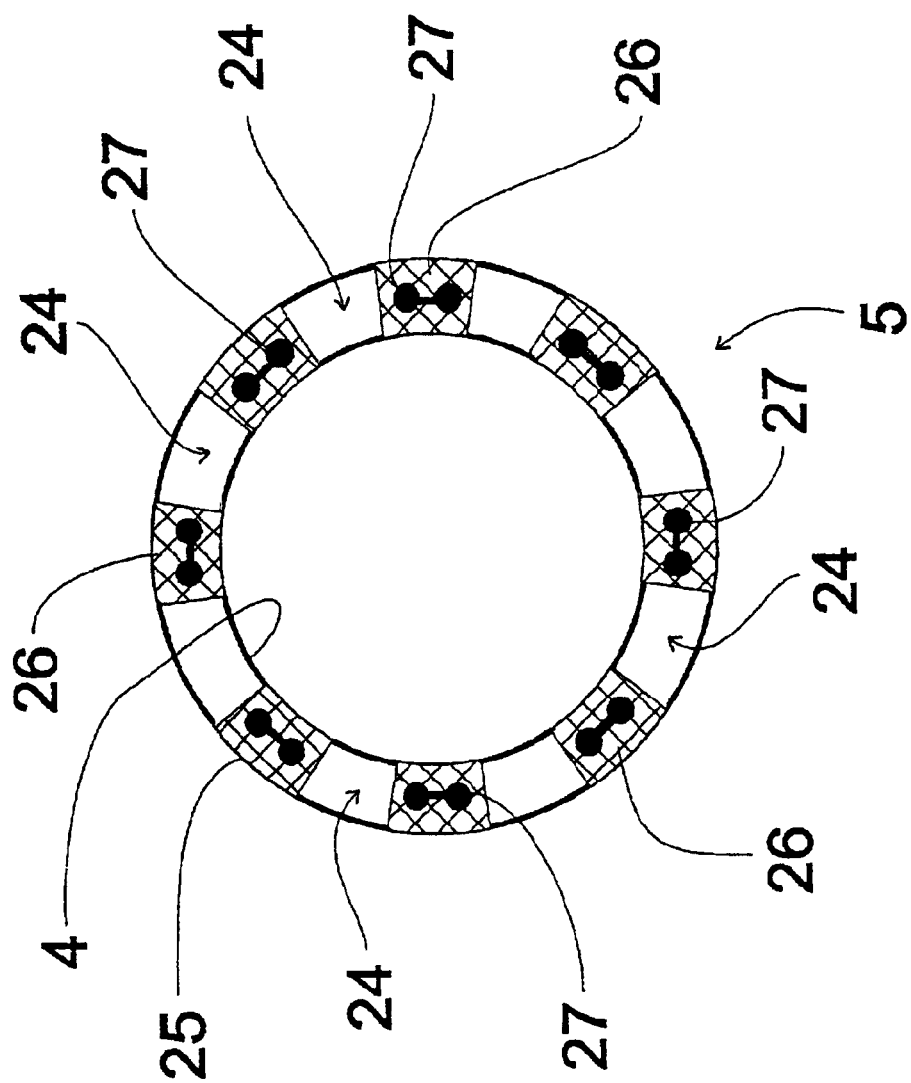
FIG. 11 a cross section of the exemplary embodiment as illustrated in FIG. 8, equipped with a reinforcement structure that is attached to the bridges that are formed between the grooves.

FIG. 11 shows a cross section of the bypass section 5 from the exemplary embodiment as illustrated in FIG. 8 and in FIG. 9, or the related modification as illustrated in FIG. 10. As can be seen in FIG. 11, a reinforcement structure 27 is integrated into the bridges 26, being formed, for example, from wire, mesh netting, or rigid plastic inserts; this reinforcement structure serves to ensure a high level of resistance to torsion for the bypass section 5.

During a positioning of the balloon 10 in the bypass section 5 in accordance with FIG. 8 or FIG. 10, the hydraulic cross section is now expanded via the grooves 24 in order to allow a sufficient quantity of fluid to flow through. Hence, a sufficient quantity of fluid, such as contrast medium, can flow past even an inner wall of the guide catheter 4 that is lying close to an unexpanded balloon 10, in order to allow imaging of the vessel that is to be handled or treated.

Figure 12:
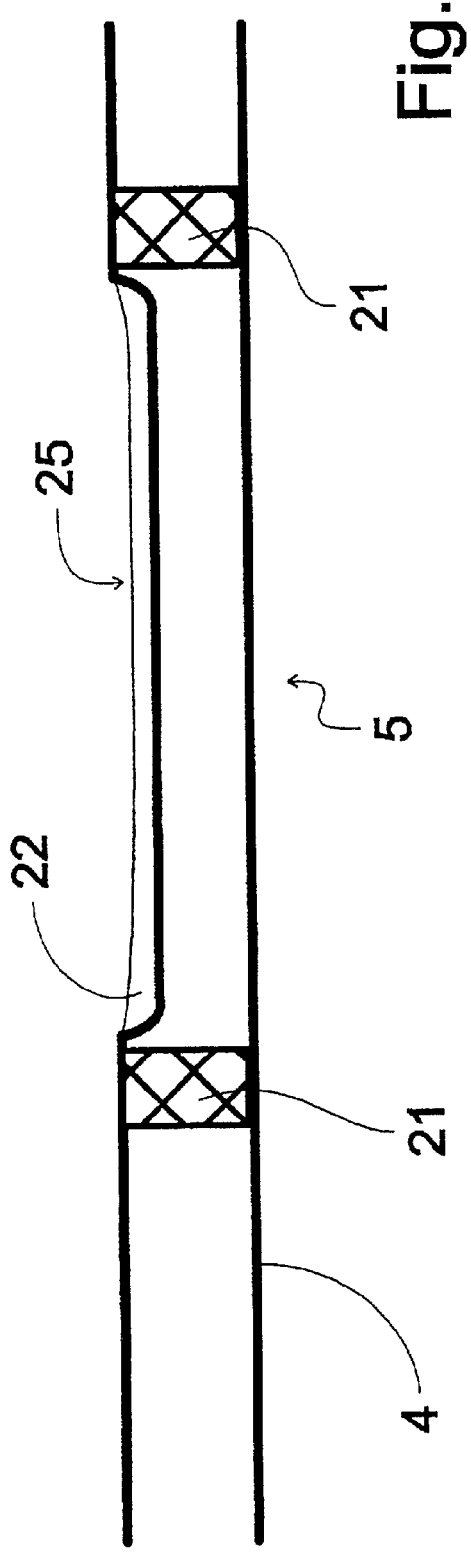
FIG. 12 a partial side view cross section of a seventh exemplary embodiment of the invention, with a section of a guide catheter containing a recess in its wall in the area of the bypass section, with this recess being sealed by a bypass sheath, FIG. 13 a section of the exemplary embodiment illustrated in FIG. 12 in the area of the bypass section, in which the bypass sheath is in an inward, engaged, initial position, FIG. 14 a partial side view cross section of a further improvement on the exemplary embodiment illustrated in FIG. 12, with a sheath frame unit that extends lengthwise along the recess in the wall, and is in an inward, engaged, initial position, FIG. 15 a section through the embodiment of the further improvement illustrated in FIG. 14, having a sheath frame unit comprised of two frame braces that is in its inward, engaged, initial position, FIG. 16 a section through a further embodiment of the further improvement illustrated in FIG. 14, having a sheath frame unit comprised of a frame membrane that is in its inward, engaged, initial position, FIG. 17 a section through the embodiment illustrated in FIG. 15 of the further improvement illustrated in FIG. 14, in the area of the bypass section, during insertion though an insertion valve, FIG. 18 a partial side view cross section of the seventh exemplary embodiment as illustrated in FIG. 12, with the bypass sheath in its outward, disengaged, secondary position, FIG. 19 a section through the exemplary embodiment as illustrated in FIG. 12, in the area of the bypass section, with a bypass sheath that is in its outward, disengaged, secondary position, FIG. 20 a section through the embodiment illustrated in FIG. 15 with the frame braces in their outward, disengaged, secondary position, FIG. 21 a section through the embodiment illustrated in FIG. 16 with the frame membrane in its outward, disengaged, secondary position, FIG. 22 a partial side view cross section of an eighth exemplary embodiment of the invention, with a section of a guide catheter having a pre-expanded bypass section, and FIG. 23 a lengthwise cross section of an insertion valve with a guide catheter that has already been introduced and has a pre-expanded bypass section.

FIG. 12 shows a partial side view cross section of a seventh exemplary embodiment of the invention, with a section of a guide catheter 4. In the area of the bypass section 5, which is preferably implemented as a separate, highly torsion-resistant, intermediate section, a wall recess 25 is provided, which is sealed off by a collapsible bypass sheath 22. The bypass sheath 22 is attached to the wall along the edge of the wall recess 25. Further, the guide catheter 4 in the seventh exemplary embodiment is equipped with edge markers 21, which are positioned at the end of the bypass section 5.

Figure 13:
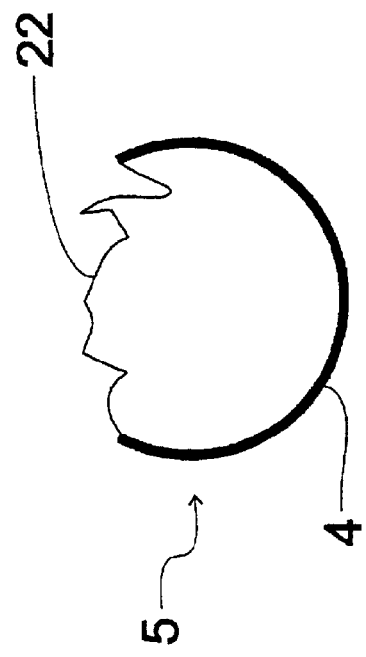

FIG. 13 shows a section through the exemplary embodiment illustrated in FIG. 12, in the area of the bypass section 5. In the arrangement shown in FIG. 13, the bypass sheath 22 is collapsed, so that it is positioned within the guide catheter 4, in an inward, engaged position.

Figure 14:
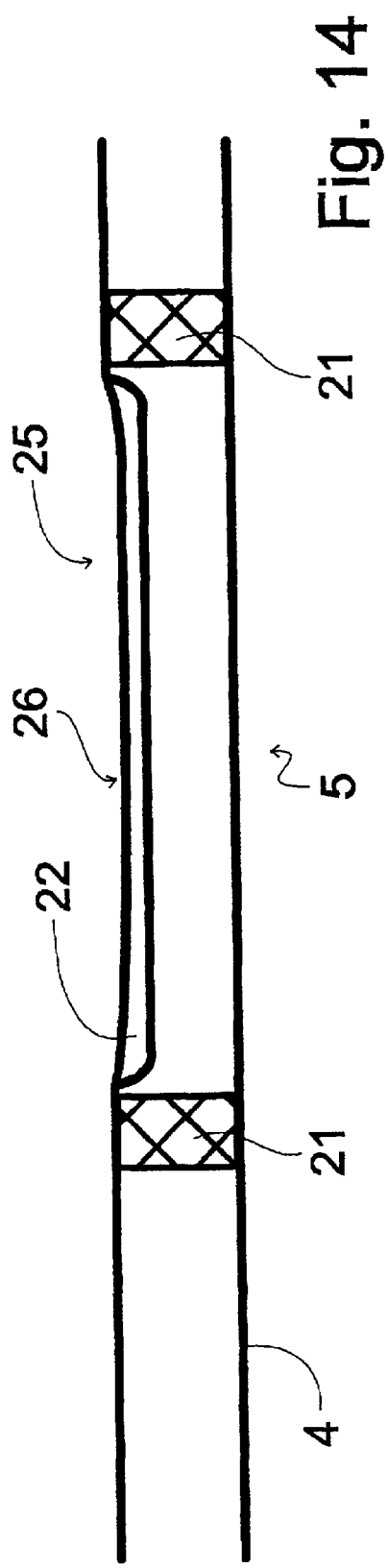

FIG. 14 shows a partial side view cross section of a further improvement on the exemplary embodiment illustrated in FIG. 12, with a sheath frame unit 26 that extends along the wall recess 25 in an inward, engaged, initial position. In this initial position, the sheath frame unit 26 is turned inward, in the direction of the inner surface of the guide catheter 4. The sheath frame unit 26 provides reinforcement for the guide catheter 4 in the area of the bypass section 5.

Figure 15:

FIG. 15 shows a section through an embodiment of the further improvement as illustrated in FIG. 14, with a sheath frame unit 26 comprised of two frame braces that is in the inward, engaged, initial position. The frame braces 27 extend lengthwise along the guide catheter 4, over the entire length of the wall recess 25, and are rectangular in cross section, which serves to ensure that the frame braces 27 will move in essentially a radial direction, even if the force exerted upon them is not exclusively radial. In this embodiment, the bypass sheath 22 is connected to the guide catheter 4 only along the edges of the wall recess 25, so that the wall recess 25 and the frame braces 27 can move independently of one another.

Figure 16:
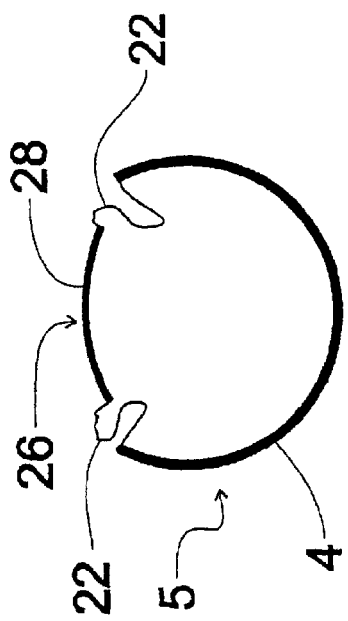

FIG. 16 shows a section through a further embodiment of the further improvement as illustrated in FIG. 14, having a sheath frame unit 26 comprised of a frame membrane 28 that is in its inward, engaged, initial position. The flattened frame membrane 28 is designed to be radially curved, and has a radius of curvature that corresponds to the radius of curvature of the guide catheter 4. The frame membrane 28 preferably extends over at least half of the radial dimensions of the wall recess 25. In the embodiment illustrated in FIG. 16, the bypass sheath 22 is attached both to the edges of the wall recess 25 and to the lengthwise edges of the frame membrane 28 such that a seal is formed.

Figure 17:
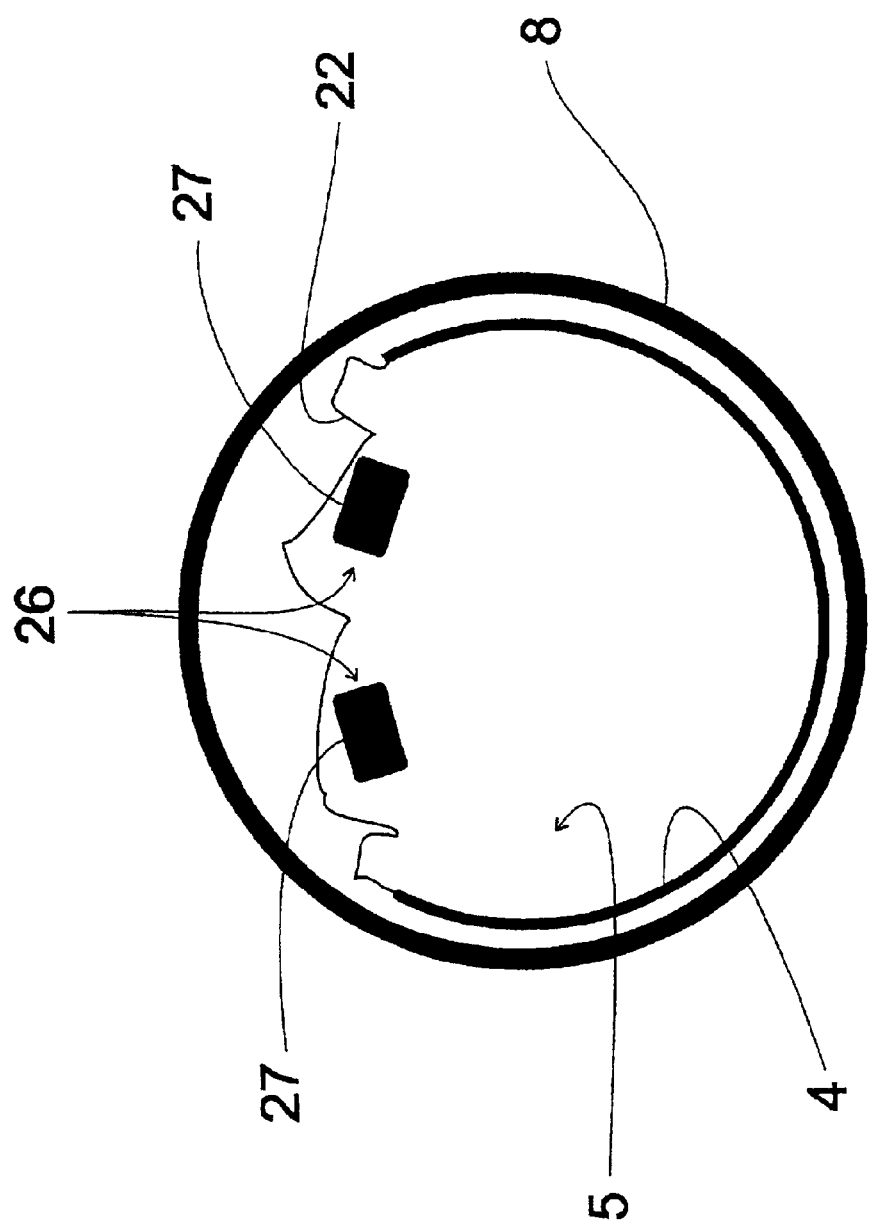

FIG. 17 shows a section through the embodiment illustrated in FIG. 15 of the further improvement on the seventh exemplary embodiment as illustrated in FIG. 14 in the area of the bypass section 5, during insertion through an insertion valve 8. As can be seen in FIG. 17, in the inward, engaged, initial position of the frame braces 27, the outside diameter of the guide catheter 4 in the area of the bypass section 5 corresponds essentially to the inside diameter of the insertion valve 8.

Figure 18:
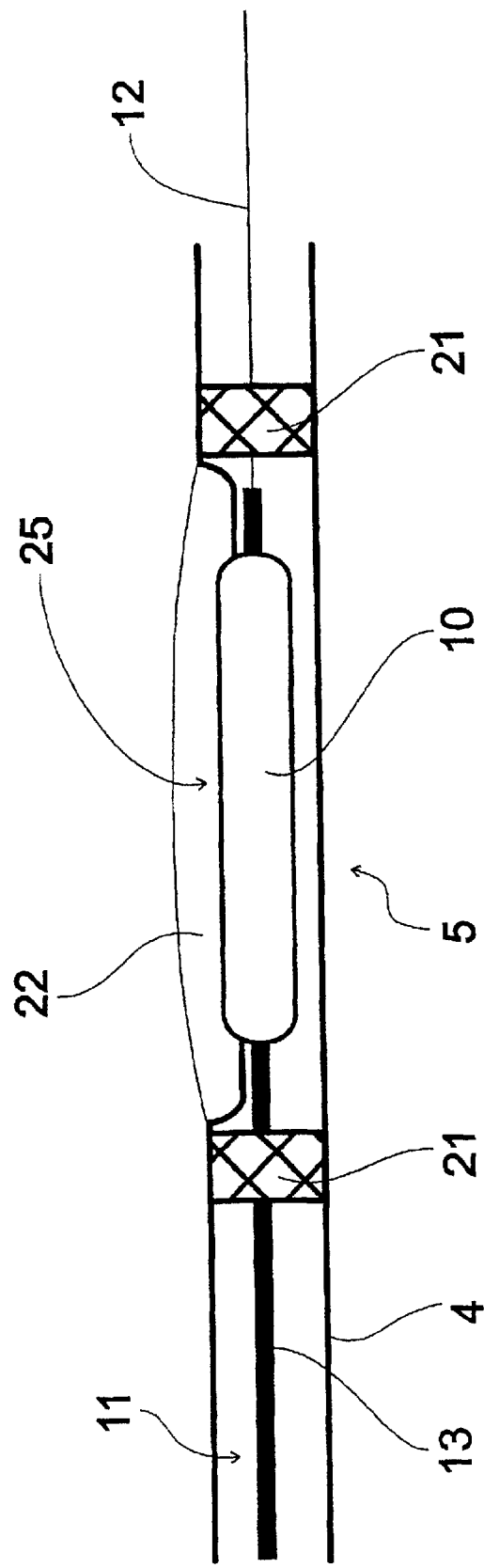

FIG. 18 shows a partial side view cross section of the seventh exemplary embodiment as illustrated in FIG. 12, with the bypass sheath 22 in an outward, disengaged, unfolded, secondary position. In the illustration in FIG. 18, a balloon 10 is positioned in the area of the bypass section 5 as the instrument. The unfolding of the bypass sheath 22 can be achieved via pressure from the fluid that is introduced into the guide catheter 4, and/or via dilation of the balloon 10.

FIG. 19 shows a section through the seventh exemplary embodiment as illustrated in FIG. 12, in the area of the bypass section 5, with an outward, disengaged, unfolded, bypass sheath 22. With the unfolding of the bypass sheath 22, the hydraulic cross section of the guide catheter 4 in the area of the bypass section 5 is expanded, so that sufficient fluid can be introduced into the vascular area that is to be treated or has been treated using diagnostic or therapeutic micro-invasive surgical procedures.

FIG. 20 shows a section through the embodiment illustrated in FIG. 15 with the frame braces 27 in an outward, disengaged, swiveled, secondary position. When the frame braces 27 are swung outward, which occurs as a result of the essentially radial flexibility of the cross section, the bypass section 22 becomes unfolded, and at the same time is stabilized against unintentional collapse, so that after it is disengaged, an expanded hydraulic cross section for the bypass section 5 is ensured during the remainder of the micro-invasive surgical procedure.

FIG. 21 shows a section through the embodiment as illustrated in FIG. 16 with the frame membrane 28 in an outward, disengaged, secondary position. Due to the connection of the bypass sheath 22 to the frame membrane 28 in this embodiment, when the frame membrane 28 is in the outward, disengaged, secondary position, the bypass sheath 22 is essentially pulled taut, so that fluid is permitted to flow through the bypass section 5, with its expanded cross section, essentially without turbulence.

Figure 22:
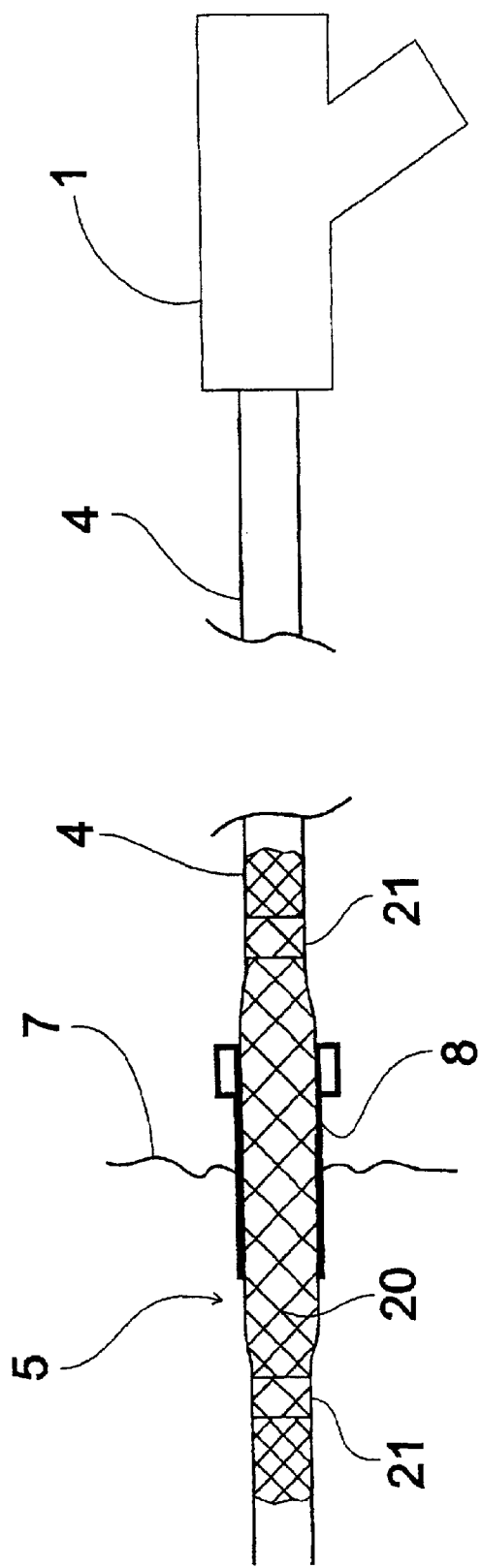

FIG. 22 shows a partial side view cross section of an eighth exemplary embodiment of the invention with a section of a guide catheter 4 having a pre-expanded bypass section, in other words a bypass section that has been expanded prior to its initial use or even during production. In keeping with the fourth exemplary embodiment described in connection with FIG. 4 and FIG. 6, the guide catheter 4 of the eighth exemplary embodiment is equipped with a reinforcement structure 20 that is incorporated into the wall, in the area of the bypass section 5; this reinforcement structure, however, deviates from that of the fourth exemplary embodiment in that it is expanded prior to its introduction through the insertion valve 8.

In one implementation of the eighth exemplary embodiment, the bypass section 5 is designed such that it is relatively flexible radially, so that during introduction through an insertion valve 8, which is designed to be relatively rigid radially, the wall of the guide catheter 4 and the reinforcement structure collapse, and after emerging from the insertion valve 8 inside the body of the patient, again assume their original, pre-expanded dimensions.

In another implementation of the eighth exemplary embodiment, the bypass section 5 is designed to be relatively rigid radially, while the insertion valve 8 is relatively flexible radially. During introduction of the relatively rigid, pre-expanded bypass section 5 through the insertion valve 8, the insertion valve 8 expands briefly without causing significant trauma to the surrounding tissue wall 7, and afterward returns to its original cross section.

It is understood that these two implementations are to be viewed as extreme cases, and that any intermediate implementations in which the bypass section 5 is somewhat flexible radially, and the insertion valve 8 is correspondingly somewhat flexible radially, with the bypass section 5 being more flexible the more rigid the insertion valve 8 is, and vice versa, are possible.

Figure 23:
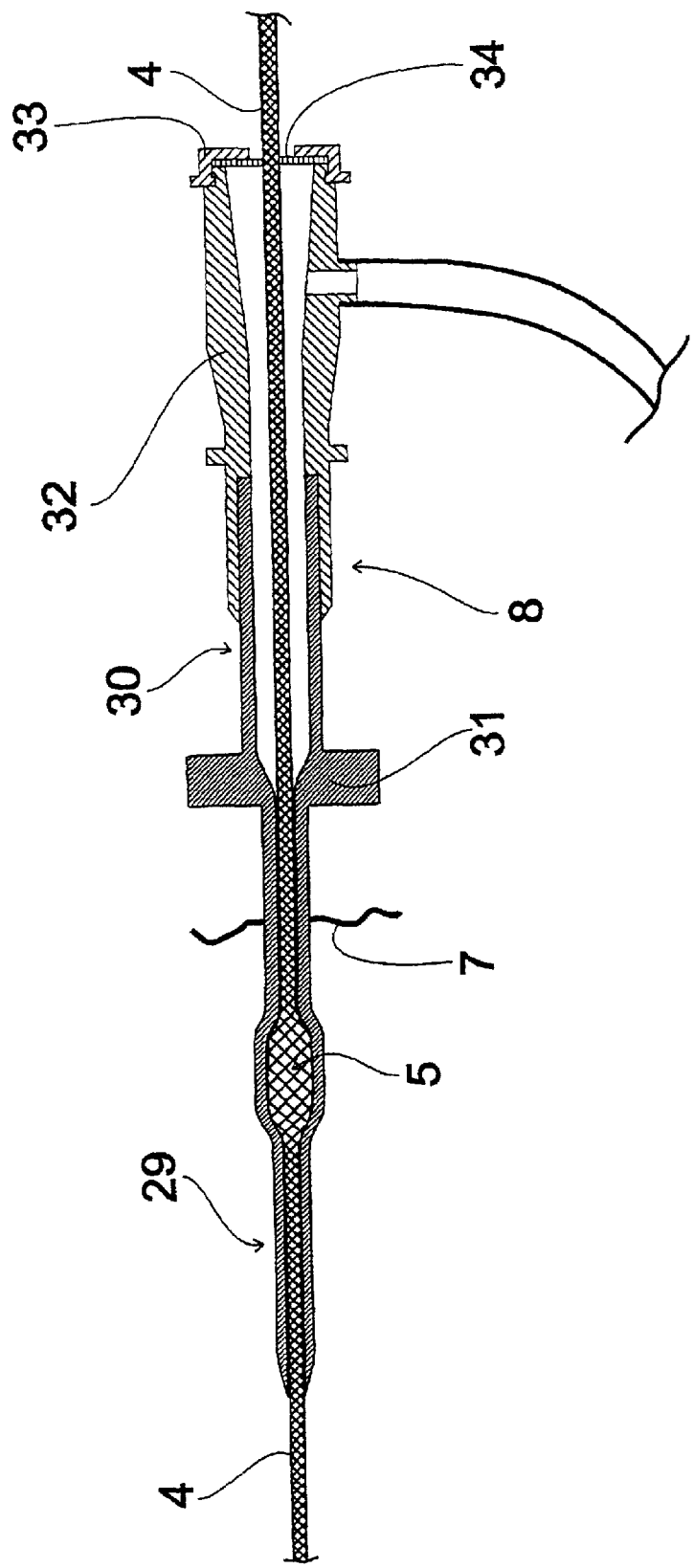

FIG. 23 shows a lengthwise cross section of an insertion valve 8 with a guide catheter 4 that has already been introduced and has a pre-expanded bypass section 5. The bypass section 5 lies between the proximal end and the distal end of the guide catheter 4. The insertion valve 8 as illustrated in FIG. 23 is equipped with a distal section 29 whose inner cross section corresponds essentially to the outer cross section of the guide catheter 4 on both sides of the bypass section 5. The insertion valve 8 is further equipped with a proximal section 30, whose inner cross section corresponds essentially to the outer cross section of the bypass section 5. In the area between the proximal section 30 and the distal section 29 of the insertion valve 8, a constant tapering of the inner cross section is provided. The tapered area is preferably designed to have on its outer surface a thickened area 31, designed to prevent, to the greatest extent possible, an unintended expansion of the trauma to the tissue wall 7. At least the distal section 29 of the insertion valve 8 is designed to be radially flexible, so that the bypass section 5 can be introduced through the insertion valve 8 with the expansion of the distal section 29. The proximal section 30 is connected to a base 32 of the insertion valve 8, which in FIG. 23 is disproportionately large, to which a sealing membrane 34 can be attached via a screw 33.

What is claimed is:

1. Device for use in micro-invasive surgical procedures, comprising:
    a valve unit,
    a guide catheter connected to the valve unit, an instrument catheter, fitted with an instrument can be inserted through the valve unit into the guide catheter,
    wherein a guide shaft (13), into which a guide wire (12) is inserted, is connected to the instrument, and the guide wire (12) proximally emerges from the guide catheter at a proximal point of exit and the guide wire distally emerges from a distal end of the instrument, the distal end of the instrument being distal to a distal end of the guide shaft,
    a hydraulic bypass section (5) is provided as a proximal end section of the guide catheter (4), wherein the hydraulic bypass section (5) is positioned distal to the valve unit (1), and
    wherein, while at least part of the wall of the guide catheter (4) is close-fitting for the instrument (10), and a lumen cross section of the guide catheter corresponds essentially to a largest cross section of the instrument (10), a hydraulic bypass cross section of the hydraulic bypass section is larger than the lumen cross section, and
    the length of the hydraulic bypass section having the larger cross section corresponds to at least the length of the section of the instrument having the largest cross section, and
    the total length of the hydraulic bypass section (5) and the valve unit (1) is greater than the distance between the distal end of the instrument (10) and the proximal point of exit of the guide wire (12).

2. Device in accordance with claim 1, wherein the bypass section (5) is integrated into the guide catheter (4).

3. Device in accordance with claim 1, wherein the instrument (10) comprises a dilatable balloon (10).

4. Device in accordance with claim 1, wherein the bypass section (5) is designed to form a singe piece with the valve unit (1).

5. Device in accordance with claim 1, wherein the bypass section (5) is designed as an intermediate segment (18) that can be inserted between the guide catheter (4) and the valve unit (1).

6. Device in accordance with claim 5, wherein the intermediate segment (18) can be connected to the guide catheter (4) such that it can rotate.

7. Device in accordance with claim 3, wherein the bypass section (5) is either entirely transparent, or transparent in at least one partial section.

8. Guide catheter (4) for a device for use in micro-invasive surgical procedures, into which an instrument catheter fitted with an instrument (10) can be inserted through a valve unit in the device, the instrument (10) being connected to a guide shaft (13) into which a guide wire (12) is inserted, the guide wire proximally emerging from the guide catheter at a proximal point of exit and the guide wire distally emerging from a distal end of the instrument, the distal end of the instrument being distal to a distal end of the guide shaft, the guide catheter comprising:
    a hydraulic bypass section (5) is provided as a proximal end section of the guide catheter (4), wherein the hydraulic bypass section (5) is positionable distal to the valve unit (1),
    wherein, while at least part of the wall of the guide catheter (4) is close-fitting for the instrument, and a lumen cross section of the guide catheter corresponds essentially to a largest cross section of the instrument (10), a hydraulic bypass cross section of the bypass section is larger than the lumen cross section, and
    the length of the hydraulic bypass section having the larger cross section corresponds to at least the length of the section of the instrument having the largest cross section, and
    the total length of the bypass section (5) and the valve unit (1) is greater than the distance between the distal end of the instrument (10) and the proximal point of exit of the guide wire (12).

9. Guide catheter in accordance with claim 8, wherein the instrument (10) comprises a dilatable balloon (10).

10. Method for use in micro-invasive surgical procedures, wherein an instrument catheter (11) fitted with an instrument (10) can be inserted through a close-fitting guide catheter (4) in the body of a patient, until it reaches an area in which diagnostic and/or therapeutic procedures are to be performed, the method comprising:
    positioning the instrument (10) during the micro-invasive surgical procedure inside a bypass section (5), whose hydraulic cross section is larger than a lumen cross section of the guide catheter (4), and whose length corresponds to at least the length of the instrument (10) wherein the bypass section is provided as a proximal end section of the guide catheter and is positioned distal to a valve unit, and
    introducing a fluid into the guide catheter (4) when the instrument (10) has been positioned inside the bypass section (5).

11. Method in accordance with claim 10, wherein the hydraulic cross section is expanded via an instrument, designed as a dilatable balloon (10).

* * * * *